US00PP13979P39

(12) United States Plant Patent
Bessho

(10) Patent No.: US PP13,979 P3
(45) Date of Patent: Jul. 15, 2003

(54) PETUNIA PLANT NAMED 'KAKEGAWA S59'

(75) Inventor: Masao Bessho, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 09/989,537

(22) Filed: Nov. 21, 2001

(65) Prior Publication Data

US 2003/0097698 P1 May 22, 2003

(51) Int. Cl.[7] ..... A01H 5/00
(52) U.S. Cl. ..... Plt./356
(58) Field of Search ..... Plt./356

(56) References Cited

U.S. PATENT DOCUMENTS

PP10,029 P * 9/1997 Rother ..... Plt./356
PP11,825 P2 * 3/2001 Heffner ..... Plt./356

OTHER PUBLICATIONS

UPOV–ROM GTITM Computer Database, 2002/03, GTI Jouve Retrieval Software, citation for 'Kakegawa S59'.*

* cited by examiner

*Primary Examiner*—Bruce R. Campell
*Assistant Examiner*—Susan B. McCormick
(74) *Attorney, Agent, or Firm*—Jondle & Associates PC

(57) ABSTRACT

A Petunia plant particularly distinguished by its pink flower color and creeping, mounding habit.

1 Drawing Sheet

GENUS AND SPECIES

*Petunia hybrida.*

VARIETY DENOMINATION

'Kakegawa S59'.

BACKGROUND OF THE NEW PLANT

The present invention comprises a new and distinct cultivar of Petunia, botanically known as *Petunia hybrida,* and hereinafter referred to by the cultivar name 'Kakegawa S59'. 'Kakegawa S59' originated from a hybridization made in 1997 in Kakegawa, Japan. The male parent originated from a cross made in 1992 between a dwarf multiflora pink breeding line and a small, magenta flowered breeding line with creeping habit. From a total of twenty $F_1$ plants produced, three were selected in 1993 for intercrossing. From a total of 80 $F_2$ plants, one plant with small, light pink flowers and a creeping habit was selected in fall 1993 as line 4-185F-1a. In spring 1994, 4-185F- 1a was crossed to a dwarf multiflora pink breeding line known as 9S-829-2a-1a -1a-1. Three plants were selected from the $F_1$ seed and intercrossed to produce $F_2$ seed. In 1995 a large, pink flowered plant with creeping habit was selected and over the next two years single plant selection was used to self the male parent to the $F_4$ generation. In 1997, 'Kakegawa S59's' male parent was crossed again to the female parent, dwarf multiflora pink breeding line 9S-829-2a-1a-1a-1.

Two hundred $F_1$ plants were transplanted to the field in Salinas, Calif. during the summer of 1998. Four lines were selected for further evaluation and vegetatively propagated. The four lines were propagated again in 1999 and evaluated for fixed characteristics and ease of propagation. Final selection of one line was made in Salinas, Calif. during the summer of 1999. The line was established as 'Kakegawa S59', and determined to have its characteristics firmly fixed.

'Kakegawa S59' has been found to retain its distinctive characteristics after two years and four cycles of vegetative propagation and this novelty is firmly fixed. The variety has demonstrated stability during this time and has no inherent variation or off-types.

DESCRIPTION OF PHOTOGRAPH

This new Petunia plant is illustrated by the accompanying photograph which shows blooms, and foliage of the plant in full color, the colors shown being as true as can be reasonably obtained by conventional photographic procedures.

DESCRIPTION OF THE NEW CULTIVAR

Figure 1:
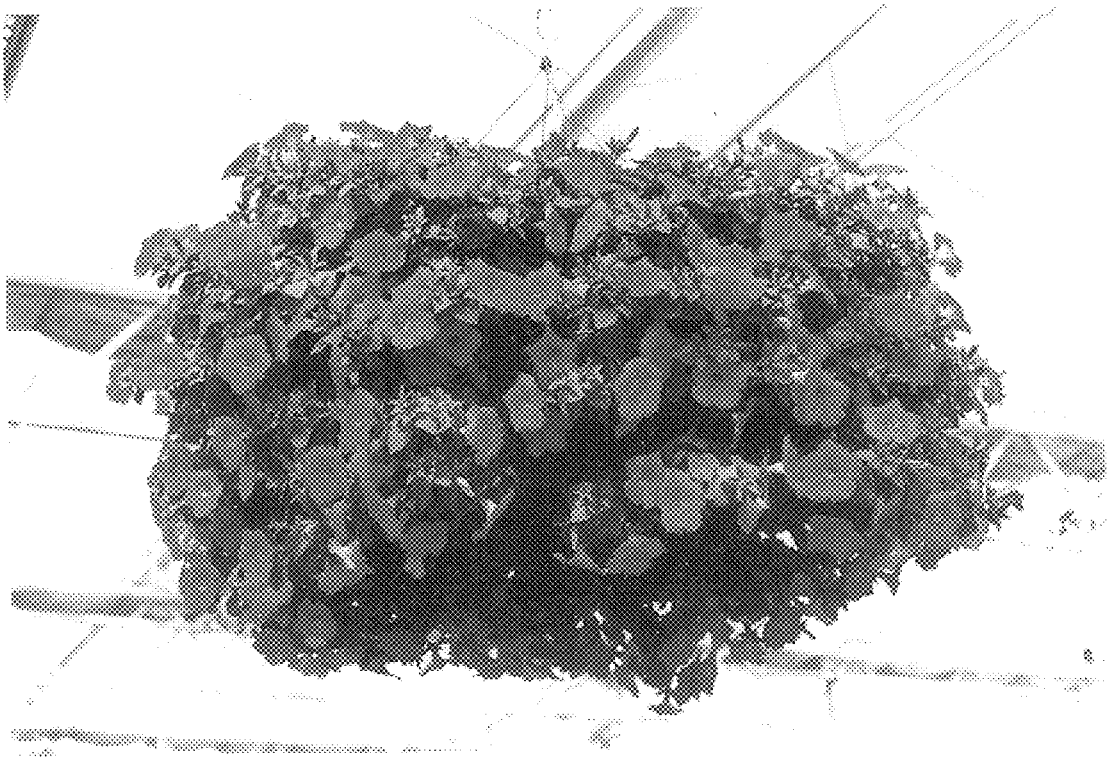
FIG. 1 shows the entire plant approximately eight weeks after transplanting a rooted cutting.
Figure 2:
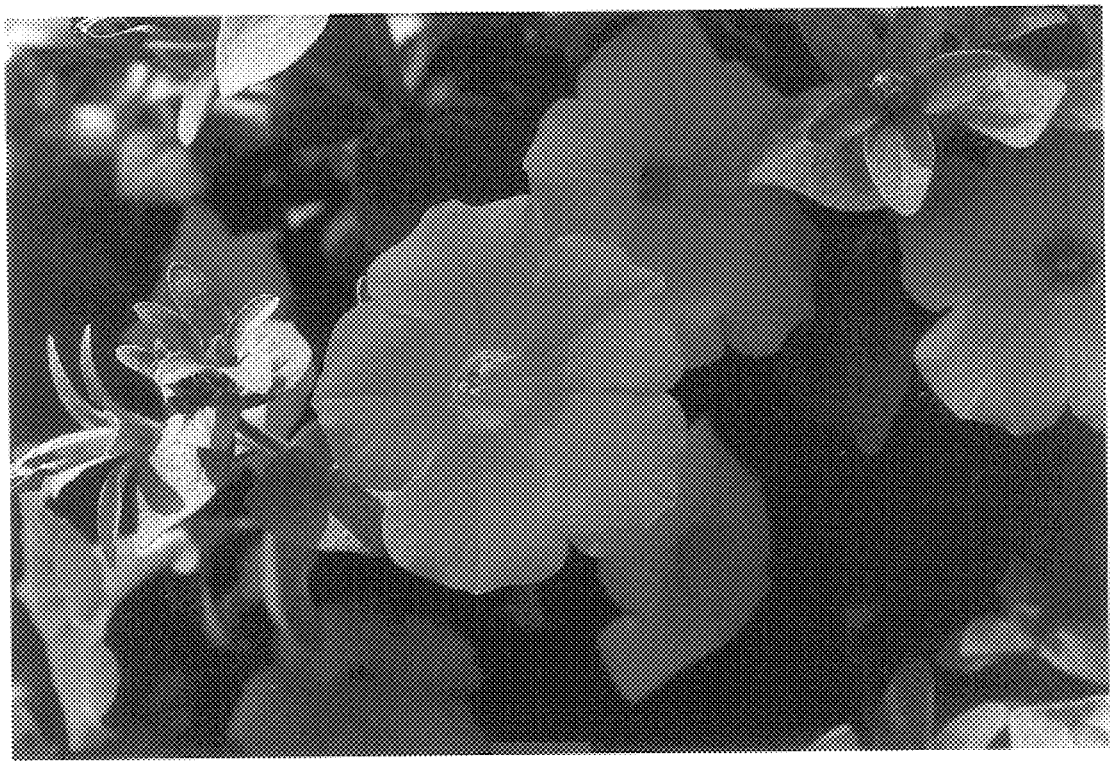
FIG. 2 shows the mature inflorescence.

The following detailed descriptions set forth the distinctive characteristics of 'Kakegawa S59'. The data which defines these characteristics were collected from asexual reproductions carried out in Salinas, Calif. Three plants from fully rooted 15 cm diameter pots were transplanted to one 50 cm diameter hanging baskets and grown in the same conditions. Data was collected on plants in 50 cm diameter pots eight weeks after rooted cuttings were transplanted. Color references are primarily to The R.H.S. Colour Chart of The Royal Horticultural Society of London (R.H.S.).

DESCRIPTION OF THE NEW PLANT

Classification:
*Botanical.*—*Petunia hybrida.*
*Commercial.*—Petunia.

Parentage:
*Female parent.*—Breeding line 9S-829-2a-1a-1a-1 (not patented).
*Male parent.*—An $F_4$ selection from a cross between breeding lines 92-829-2a-1a-1a-1 (not patented) and 4-185F-1a (not patented).

Environmental conditions for plant growth: Plants were propagated from vegetative cuttings, and grown individually in 15 cm diameter plastic pots in a glass greenhouse located in Salinas, Calif. Pots contained a peat moss-based growing medium. Soluble fertilizer containing 18% nitrogen, 8% phosphorus and 18% potassium was applied in four, daily irrigations. The fifth irrigation was made with non-fertilized water. Pots were top-dressed with a slow release fertilizer containing 18% nitrogen, 8% phosphorus and 18% potassium. The typical average air temperature was 24C.

Growth:

*Habit.*—Branching, creeping.

*Form.*—Descending.

*Plant size.*—45 cm total diameter and 25 cm total height.

*Flowering habit.*—Indeterminate.

*Time to initiate root development.*—7 days after sticking cuttings.

*Time to bloom from propagation.*—4–6 weeks after rooting when grown in 10–15 cm diameter plastic pots.

*Life cycle.*—Annual.

Stems:

*Color.*—Yellow-green (RHS 146A).

*Description.*—Round.

*Diameter.*—0.4 to 0.5 mm.

*Internode length.*—3.0–4.0 cm.

Leaves:

*Arrangement.*—Opposite.

*Apex.*—Mucronate.

*Base.*—Oblique.

*Color.*—Upper surface is green (RHS 139B) and lower surface is green (RHS 138C).

*Margin.*—Entire.

*Size.*—Length is 4.8 cm and width is 4.5–5.0 cm.

*Shape.*—Ovate.

*Texture.*—Coarse.

*Venation.*—Pinnate.

*Pubescence.*—Present, clear.

Buds:

*Bud color.*—Yellow-green (RHS 144C).

*Bud diameter.*—5.0 mm.

*Bud length.*—1.8 cm.

Flowers:

*Calyx.*—5 sepals; 2.3 cm×0.5 cm (length×width).

*Corolla.*—5 petals, fused.

*Flower diameter.*—6.0–7.0 cm.

*Fragrant.*—Yes.

*Inflorescence type.*—Solitary.

*Pistil.*—Compound.

*Ovary.*—Superior, parietal placentation.

*Stamens.*—5 total with two long and three short; red-purple (RHS 62B).

*Style.*—Green (RHS 143C).

*Peduncle.*—2.5–3.0 cm×0.2 mm (length×width); pubescent.

*Petal color.*—Limbs: upper — red-purple (RHS 74B); lower — red-purple (RHS 73A). Tube — Inner — red-purple (RHS 73C); Outside is red-purple (RHS 69C) with green (RHS 141C) veins.

*Petal margin.*—Smooth.

*Petal pubescence.*—Absent.

*Tube throat diameter.*—1.0 cm.

*Pollen color.*—White (RHS 155A).

*Produces seed.*—Yes; grey-orange (RHS 172B); <1.0 mm diameter; seed coat has netted pattern, 8–10,000 seeds/gram.

Disease and Insect Resistance

No susceptibility to diseases or insects noted to date.

Comparison with Known Cultivars

'Kakegawa S59' is most similar to the variety 'Cascadia Pink' but differs in the following areas: 'Kakegawa S59' has a true pink petal limb color where 'Cascadia Pink' is a more reddish color. The inside color for the corolla tube is white on 'Cascadia Pink' where it is a light pink on 'Kakegawa S59'.

Comparison with Parental Cultivars

Table 1 below lists some traits from the parental cultivars as compared to the present invention.

TABLE 1

| Characteristic | 'Kakegawa S60' | 9S-829-2a-1a-1a-1 (female) | 4-185F-1a (male) |
|---|---|---|---|
| Plant Habit | Creeping | Dwarf and compact | Creeping |
| Flower Size | Medium | Medium size | Small size |
| Flower Petal Color | Dark Pink | Pink | Light Pink |

I claim:

1. A new and distinct Petunia plant as shown and described herein.

* * * * *